United States Patent [19]
Zwaagstra et al.

[11] Patent Number: 6,046,212
[45] Date of Patent: Apr. 4, 2000

[54] CHALCONE DERIVATIVES AND DRUGS CONTAINING THE SAME

[75] Inventors: Maria Elizabeth Zwaagstra, Amsterdam, Netherlands; Mingqiang Zhang, Scotland, United Kingdom; Henk Timmerman, Voorschoten, Netherlands; Kazuhiro Onogi, Iruma, Japan; Masahiro Tamura; Tsutomu Toma, both of Higashimurayama, Japan; Yasushi Wada, Tachikawa, Japan

[73] Assignee: Kowa Co., Ltd., Nagoya, Japan

[21] Appl. No.: 09/147,270

[22] PCT Filed: May 16, 1997

[86] PCT No.: PCT/JP97/01652

§ 371 Date: Nov. 17, 1998

§ 102(e) Date: Nov. 17, 1998

[87] PCT Pub. No.: WO97/44306

PCT Pub. Date: Nov. 27, 1997

[30] Foreign Application Priority Data

May 17, 1996 [JP] Japan .................................. 8-122910
Oct. 1, 1996 [JP] Japan .................................. 8-260673

[51] Int. Cl.⁷ .............. C07D 215/12; C07D 277/60; C07D 263/62; C07D 235/04; C07D 235/12

[52] U.S. Cl. .............. 514/311; 514/314; 514/367; 514/375; 514/414; 514/419; 546/174; 548/180; 548/219; 548/304.7; 548/310.1

[58] Field of Search .................. 514/311, 314, 514/367, 375, 414, 419; 546/174; 548/180, 219, 304.7, 310.1

[56] References Cited

FOREIGN PATENT DOCUMENTS 0 834 510 A2  4/1998  European Pat. Off. .
WO 89/04303  5/1989  WIPO .

OTHER PUBLICATIONS

Chemical Abstracts 125:275456, 1995.

Chemical Abstracts 122:133214, 1994.

Chemical Abstracts 124:8860, 1995.

Mauriel e. Zwaagstra et al, "Synthesis and Structure—Activity Relationships of Carboxylated Chalcones: A Novel Series of $CysLT_1$ ($LTD_4$) Receptor Antagonists", J. Med. Chem., vol. 40, pp. 1075–1089 (1997).

*Primary Examiner*—D. Margaret Seaman
*Attorney, Agent, or Firm*—Oblon, Spivak, McClelland, Maier & Neustadt, P.C.

[57] ABSTRACT

This invention relates to chalcone derivatives represented by the following formula (1):

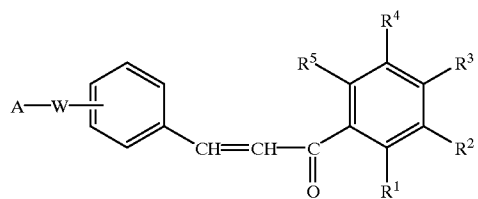

wherein A represents a phenyl group, a quinolyl group or the like, W represents a vinylene group or the like, and $R^1$ to $R^5$ each independently represent a carboxyl, cyano, alkyloxycarbonyl or like group, or salts of the chalcone derivatives, and also to drugs containing them as effective ingredients. These compounds have excellent cys-LT receptor antagonism, and are useful as antiallergic agents or the like.

8 Claims, No Drawings

CHALCONE DERIVATIVES AND DRUGS CONTAINING THE SAME

This application is a 371 of PCT/JP97/01652, filed May 16, 1997.

TECHNICAL FIELD

This invention relates to chalcone derivatives having excellent antagonism to cys-leukotriene receptors and drugs containing the same.

BACKGROUND ART

Peptidoleukotrienes (LT) are a group of physiologically-active substances synthesized from eicosapolyenoic acids such as arachidonic acid in animal tissues. Among these, $LTC_4$, $LTD_4$ and $LTE_4$ are known to act as important causal substances for bronchial asthma both in vitro and in vivo (Henderson, W. R., Jr. Ann. Intern. Med., 121, 684–697, 1994). As morbid conditions caused by these leukotrienes, there are airway constriction, mucosal oversecretion and pulmonary edema. They eventually induce an airway disorder which is a characteristic of asthma. Effects of $LTC_4$ or $LTD_4$ on airway constriction when inhaled reach 1,000 times as much as those of histamine. $LTE_4$ has lower activities compared with the other leukotrienes, but airway constriction induced by $LTE_4$ is long lasting compared with that caused by the other leukotrienes (Larsen, J. S., Acosta, E. P. Ann. Pharmacother, 27, 898–903, 1993).

Keeping in step with discovery of roles of leukotrienes in biosynthesis pathways and diseases as mentioned above, there are increasing activities for the development of synthesis inhibitors for leukotrienes, antagonists to cys-leukotriene (cys-LT) receptors and the like with a view to inhibiting leukotrienes (Metters, K. M., J. Lipid Mediators Cell Signalling, 12, 413–427, 1995). According to some recent reports in clinical aspects, it has been indicated that cys-LT receptor antagonists are extremely effective for various types of asthma (Taylor, I. K., Thorax, 50, 1005–1010, 1995; Pauwels, R. A., Joos, G. F., Kips. J. C. Allergy, 30, 615–622, 1995).

It is however the current situation that no compound has been found to have fully satisfactory cys-LT receptor antagonism.

An object of the present invention is therefore to provide a compound having a high cys-LT receptor antagonism and a drug containing the compound.

DISCLOSURE OF THE INVENTION

With the foregoing circumstances in view, the present inventors have proceeded with extensive research in attempts to obtain a compound having a high cys-LT receptor antagonism. As a result, a novel compound represented by the below-described formula (1) has been found to have a high cys-LT receptor antagonism and hence to be useful as a drug, leading to the completion of the present invention.

The present invention therefore provides a chalcone derivative represented by the following formula (1):

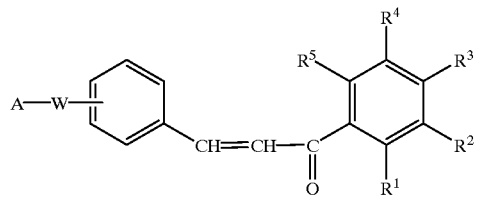

wherein
A represents a substituted or unsubstituted phenyl group, a substituted or unsubstituted naphthyl group, or a group

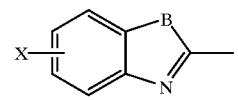

in which X represents a hydrogen or halogen atom or a hydroxyl, lower alkyl or lower alkoxyl group and B represents —CH=CH—, —N($R^6$)—, $R^6$ being a lower alkyl group or a lower alkoxyalkyl group, —O— or —S—, W represents —CH=CH— or —$CH_2$O—, and $R^1$, $R^2$, $R^3$, $R^4$ and $R^5$ may be the same or different and each independently represent a hydrogen or halogen atom, a hydroxyl, a lower alkyl, lower alkoxyl, carboxyl, cyano, alkyloxycarbonyl or tetrazolyl group, a group —$CONHR^7$ in which $R^7$ represents a hydrogen atom or a lower alkyl group, or a group —$O(CH_2)_n R^8$ in which $R^8$ represents a carboxyl, alkyloxycarbonyl or tetrazolyl group and n stands for a number of from 1 to 4, with the proviso that at least one of the groups $R^1$, $R^2$, $R^3$, $R^4$ and $R^5$ represents a carboxyl, cyano, alkyloxycarbonyl or tetrazolyl group, the group —$CONHR^7$ or the group —$O(CH_2)_n R^8$; or a salt or solvate thereof.

This invention also provides a drug comprising as an effective ingredient the chalcone derivative (1) or its salt or solvate.

Further, this invention also provides a cys-LT receptor antagonist comprising the chalcone derivative (1) or its salt or solvate as an effective ingredient.

In addition, this invention also provides an antiallergic agent comprising the chalcone derivative (1) or its salt or solvate as an effective ingredient.

Furthermore, the present invention also provides a medicinal composition comprising the chalcone derivative (1) or its salt or solvate and a pharmacologically acceptable carrier.

Moreover, the present invention also provides a treatment method of an allergic diseases, which comprises administering an effective amount of the chalcone derivative (1) or its salt or solvate.

BEST MODE FOR CARRYING OUT THE INVENTION

In the compound represented by the formula (1), illustrative of the halogen atom are fluorine, chlorine, bromine and iodine atoms. Illustrative of the lower alkyl group are linear or branched alkyl groups having 1–6 carbon atoms, specifically methyl, ethyl, n-propyl, isopropyl, n-butyl, isobutyl, t-butyl, n-pentyl and n-hexyl, with methyl, ethyl and t-butyl being particularly preferred. Illustrative of the lower alkoxyl group are linear or branched alkoxyl groups having 1–6 carbon atoms, specifically methoxy, ethoxy, linear or branched propoxy, butoxy, pentyloxy and hexyloxy, with methoxy, ethoxy, propoxy, butoxy and the like being preferred, among which methoxy is particularly preferred. Preferred examples of the lower alkoxyalkyl group include $C_{1-6}$ alkoxy $C_{1-6}$ alkyl groups, specifically methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl and the like, with ethoxyethyl being particularly preferred. Further, illustrative of the alkyloxycarbonyl group are $C_{1-6}$ alkyloxycarbonyl groups, for example, methyloxycarbonyl, ethyloxycarbonyl, propyloxycarbonyl, butyloxycarbonyl and the like, with ethyloxycarbonyl being particularly preferred.

Examples of the substituted or unsubstituted phenyl group or the substituted or unsubstituted naphthyl group represented by A in the formula (1) include a phenyl group which may be substituted by one or more halogen atoms, lower alkyl groups or lower alkoxyl groups; and a naphthyl group which may be substituted by one or more halogen atoms, lower alkyl groups or lower alkoxyl groups. Particularly preferred are phenyl and naphthyl. Illustrative of X are a hydrogen atom, halogen atoms, a hydroxyl group, lower alkyl groups and lower alkoxyl groups, with a hydrogen atom and halogen atoms being particularly preferred.

At least one of $R^1$, $R^2$, $R^3$, $R^4$ and $R^5$ represents a carboxyl group, a cyano group, an alkyloxycarbonyl group, a tetrazolyl group, a group —$CONHR^7$ or a group —$O(CH_2)_nR^8$, and the remainder thereof may be the same or different and each independently represent a hydrogen atom, a halogen atom, a hydroxyl group, a lower alkyl group or a lower alkoxyl group, a carboxyl group, a cyano group, an alkyloxycarbonyl group, a tetrazolyl group, a group —$CONHR^7$ or a group —$O(CH_2)_nR^8$. A preferred situation is that one of $R^1$, $R^2$, $R^3$, $R^4$ and $R^5$ represents a carboxyl group, a cyano group, an alkyloxycarbonyl group, a tetrazolyl group, a group —$CONHR^7$ or a group —$O(CH_2)_nR^8$ and the remainder thereof may be the same or different and each independently represent a hydrogen atom, a halogen atom, a hydroxyl group, a lower alkyl group or a lower alkoxyl group. A further preferred situation is that in the compound $R^1$ represents a hydroxyl or lower alkoxyl group.

In the group —$O(CH_2)_nR^8$, n stands for a number of from 1 to 4, preferably 1 or 2, with 1 being particularly preferred.

No particular limitation is imposed on the salt of the compound (1) of the present invention, insofar as it is a pharmacologically acceptable salt. Illustrative are metal salts such as the sodium salt, potassium salt, calcium salt, magnesium salt, manganese salt, iron salt and aluminum salt; mineral acid addition salts such as the hydrochloride, hydrobromide, hydroiodide, sulfate and phosphate; and organic acid addition salts such as the benzoate, methanesulfonate, ethanesulfonate, benzenesulfonate, p-toluenesulfonate, oxalate, maleate, fumarate, tartrate and citrate.

In addition, the compound (1) of the present invention may also exist in the form of solvates represented by the hydrate. Such solvates should also be included in the present invention.

Further, the compound (1) of the present invention may also exist in the form of a keto-enol tautomer. Such a tautomer should also be embraced in the present invention.

The compound (1) according to the present invention can be synthesized, for example, by a process indicated by the following reaction formula.

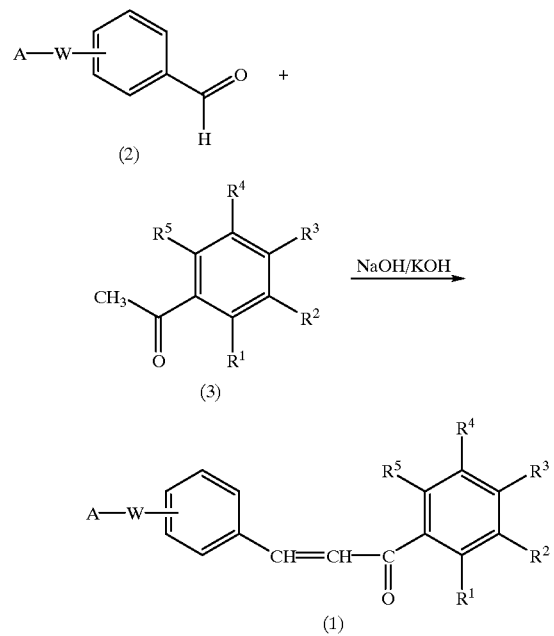

wherein A, W, $R^1$, $R^2$, $R^3$, $R^4$ and $R^5$ have the same meanings as defined above.

Described specifically, the compound (1) according to the present invention can be obtained by reacting the aldehyde derivative as the compound (2) and the acetophenone derivative as the compound (3) in the presence of a base such as sodium hydroxide or potassium hydroxide in a polar solvent such as methanol, ethanol, tetrahydrofuran or water.

The compound (2) can be obtained either by reacting a known hydroxybenzaldehyde and a chloromethylated aromatic compound when W is —$CH_2O$—, or by condensing a known dialdehyde derivative of benzene and a methylated aromatic compound in the presence of acetic anhydride.

Among compounds (3), those containing a hydroxyl group as $R^1$ and a carboxyl group or cyano group as at least one of the remaining $R^2$ to $R^5$ can each be obtained by Fries rearrangement from an acetyl derivative represented as a compound (4) in accordance with the following reaction formula.

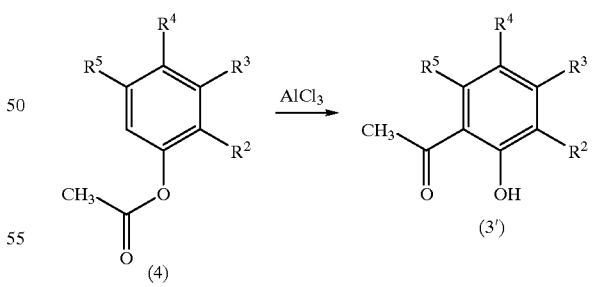

wherein $R^2$, $R^3$, $R^4$ and $R^5$ have the same meanings as defined above.

Among the compounds (3), those containing an alkyloxycarbonyl group or a tetrazolyl group as one of $R^1$ to $R^5$ can each be obtained from a corresponding carboxylic acid derivative or nitrile derivative by a method known per se in the art. For example, by refluxing a carboxylic acid derivative (a compound (3) in which at least one of $R^1$ to $R^5$ represents a carboxyl group) together with 5% sulfuric acid in an alcohol, the corresponding ester (a compound (3) in which one of $R^1$ to $R^5$ represents an alkyloxycarbonyl group) can be obtained. Further, by reacting a nitrile derivative (a compound (3) in which one of $R^1$ to $R^5$ represents a cyano group) with sodium azide in the presence of ammonium chloride in DMF, the corresponding tetrazole derivative (a compound (3) in which one of $R^1$ to $R^5$ represents a tetrazolyl group) can be obtained.

Among the compounds (3), those containing —$OCH_2CO_2CH_2CH_3$ as one of $R_1$ to $R^5$ can each be obtained by alkylation through a reaction between an appropriate hydroxyacetophenone derivative (compound (3) in which one of $R^1$ to $R^5$ is a hydroxyl group) and ethyl chloroacetate. Among the compounds (3), those containing as one of $R^1$ to $R^5$ —$OCH_2CN_4H$ in which $CN_4H$ represents a tetrazolyl group can each be obtained by first reacting an appropriate hydroxyacetophenone derivative with 2-bromoacetonitrile and then reacting the reaction product with sodium azide in the presence of ammonium chloride in DMF. Further, the compounds (3) in which one of $R^1$ to $R^5$ is an alkoxyl group can each be obtained by alkylating the corresponding hydroxy-acetophenone derivative.

The compound (1) according to the present invention can be obtained by the above-described process. Further, it can be purified by a conventional purification method such as recrystallization or column chromatography, as needed. Moreover, it can be converted into the above-described desired salt or solvate by a method known per se in the art, as needed.

The invention compound (1) or its salt or solvate obtained as described above has excellent cys-LT receptor antagonism as will be indicated in examples to be described subsequently herein, and is therefore useful as a drug for the therapy or prevention of asthma, allergic rhinitis, allergic dermatitis, allergic conjunctivitis, urticaria, psoriasis, rheumatism, inflammatory colitis, cerebral ischemia, cerebral apoplexy or the like.

The drug according to the present invention comprises the above-described compound (1) or its salt or solvate as an effective ingredient. Its unit dosage form is not limited in particular, but can be suitably chosen in accordance with the object of a therapy, for example, can be in the form of any one of oral preparations, injections, suppositories, ointments, inhalants, eye drops, nasal drops, plasters and the like. These unit dosage forms can each be prepared by a preparation method commonly known and used by those skilled in the art.

To produce an oral solid preparation, an excipient and if necessary, a binder, a disintegrator, a lubricant, a coloring matter, a taste corrigent, a smell corrigent and/or the like are added to the compound (1) of the present invention. The resulting mixture can then be formed into tablets, coated tablets, granules, powder, capsules or the like by a method known per se in the art. Such additives can be those generally employed in the present field of art, including excipients: lactose, sucrose, sodium chloride, glucose, starch, calcium carbonate, kaolin, micro-crystalline cellulose, and silicic acid; binders: water, ethanol, propanol, sucrose solution, glucose solution, starch solution, gelatin solution, carboxymethylcellulose, hydroxypropylcellulose, hydroxypropylstarch, methylcellulose, ethylcellulose, shellac, calcium phosphate, and polyvinylpyrrolidone; disintegrators: dry starch, sodium alginate, powdered agar, sodium hydrogencarbonate, calcium carbonate, sodium lauryl sulfate, monoglycerol stearate, and lactose; lubricants: purified talc, stearate salts, borax, and polyethylene glycol; corrigents: sucrose, bitter orange peel, citric acid, and tartaric acid.

To produce an oral liquid preparation, a taste corrigent, a buffer, a stabilizer, a smell corrigent and the like are added to the compound (1) of the present invention. The resulting mixture can then be formed into a solution for internal use, a syrup, an elixir or the like by a method known per se in the art. In this case, the taste corrigent can be the same as that mentioned above. Illustrative of the buffer is sodium citrate, while illustrative of the stabilizer are tragacanth, gum arabic, and gelatin.

To prepare an injection, a pH regulator, a buffer, a stabilizer, an isotonicity, a local anesthetic and the like are added to the compound (1) of the present invention. The resulting mixture can then be formed into a subcutaneous, intramuscular or intravenous injection by a method known per se in the art. Examples of the pH regulator and buffer include sodium citrate, sodium acetate, and sodium phosphate. Illustrative of the stabilizer include sodium pyrosulfite, EDTA, thioglycollic acid, and thiolactic acid. Illustrative of the local anesthetic are procaine hydrochloride and lidocaine hydrochloride. Examples of the isotonicity include sodium chloride and glucose.

To prepare suppositories, a pharmaceutical carrier known in the present field of art, for example, polyethylene glycol, lanolin, cacao butter or fatty acid triglyceride is added optionally together with a surfactant such as "Tween" (registered trademark) to the compound (1) of the present invention. The resulting mixture can then be formed into suppositories by a method known per se in the art.

To prepare an ointment, a pharmaceutical base, a stabilizer, a humectant, a preservative and the like are combined, as needed, with the compound (1) of the present invention. The resultant mixture can then be mixed and prepared into an ointment by a method known per se in the art. Illustrative of the pharmaceutical base are liquid paraffin, white petrolatum, white beewax, octyldodecyl alcohol, and paraffin. Examples of the preservative include methyl parahydroxybenzoate, ethyl parahydroxybenzoate, and propyl parahydroxybenzoate.

In addition to the above-described preparations, the compound (1) of the present invention can also be formed into an inhalant, an eye drop and a nasal drop by methods known per se in the art.

The dosage of the drug according to the present invention varies depending on the age, body weight, conditions, unit dosage form, administration frequency and the like. In general, however, it is preferred to orally or parenterally administer to an adult the effective ingredient in an amount of about 1 to 1,000 mg per day at once or in several portions.

EXAMPLES

The present invention will next be described in further detail by the following Examples. It should however be borne in mind that the present invention is by no means limited to these Examples.

Synthesis Example 1

Synthesis of 4-(2-guinolylmethoxy)benzaldehyde

A mixture of 6.42 g (0.03 mol) of 2-chloromethylquinoline hydrochloride, 3.66 g (0.03 mol) of 4-hydroxybenzaldehyde and 9.12 g (0.066 mol) of anhydrous potassium carbonate was dissolved in 50 ml of DMF, followed by heating overnight at 90° C. The reaction mixture was distilled off under reduced pressure, and the residue was extracted with ethyl acetate. The organic layer was washed with 1N NaOH and a saturated aqueous solution of sodium chloride, dried over $Na_2SO_4$ and then distilled off under reduced pressure, whereby 7.11 g of the title compound were obtained (yield: 91%).

Melting point: 81.0–82.1° C.

$^1$H-NMR(CDCl$_3$)δ(ppm): 5.41(2H,s,CH$_2$O), 7.10(2H,d, J=8.7 Hz,H3,H5), 7.47–7.51(1H,m,H6-guinoline), 7.58(1H, d,J=8.5 Hz,H3-quinoline), 7.67–7.71(1H,m,H7-quinoline), 7.74–7.79(1H,m,H5-quinoline), 7.79(2H,d,J=8.7 Hz,H2, H6), 8.07(1H,d,J=8.3 Hz,H8-guinoline), 8.15(1H,d,J=8.5 Hz,H4-guinoline), 9.86(1H,s,ArCHO).

Synthesis Example 2

Synthesis of 3-(2-quinolylmethoxy)benzaldehyde

The title compound was obtained from 3-hydroxybenzaldehyde in a similar manner as in Synthesis Example 1.

Melting point: 55.1–57.1° C.

$^1$H-NMR(CDCl$_3$)δ(ppm): 5.35(2H,s,CH$_2$O), 7.20(1H,m, H4), 7.36–7.47(3H,m,H5-quinoline,H6-quinoline,H5), 7.64–7.69(1H,m,H7-quinoline), 7.72–7.76(1H,m,H6), 8.01 (1H,d,J=8.3 Hz,H8-quinoline), 8.11(1H,d,J=8.5 Hz,H4-quinoline), 9.87(1H,s,ArCHO).

Synthesis Example 3

Synthesis of 2-(2-quinolylmethoxy)benzaldehyde

The title compound was obtained from 2-hydroxybenzaldehyde in a similar manner as in Synthesis Example 1.

$^1$H-NMR(CDCl$_3$)δ(ppm): 5.48(2H,s,CH$_2$O), 7.06(1H,d, J=8.4 Hz,H3), 7.45–7.58(2H,m,H5,H6-quinoline), 7.64(1H, d,J=8.5 Hz,H3-quinoline), 7.69–7.88(4H,m,H5-quinoline, H7-quinoline,H4,H6), 8.20(1H,d,J=8.5 Hz,H4-quinoline), 8.30(1H,d,J=8.3 Hz,H8-quinoline), 10.64(1H,s,ArCHO).

Synthesis Example 4

Synthesis of 4-[(7-chloro-2-quinolyl)methoxy]-benzaldehyde

The title compound was obtained from 7-chloro-2-chloromethylquinoline in a similar manner as in Synthesis Example 1.

Melting point: 130–133° C.

Synthesis Example 5

Synthesis of 4-[1-(2-benzothiazolyl)methoxy]-benzaldehyde

The title compound was obtained from 2-chloromethyl-1-benzothiazole in a similar manner as in Synthesis Example 1.

Melting point: 135–137° C.

$^1$H-NMR(CDCl$_3$)δ(ppm): 5.57(2H,s,CH$_2$O), 7.16(1H,d, J=8.8 Hz,H3,H5), 7.35–7.57(2H,m,H5-benzothiazole,H6-benzothiazole), 7.87(2H,d,J=8.8 Hz,H2,H6), 7.91(1H,d,J= 8.3 Hz,H4-benzothiazole), 8.06(1H,d,J=8.8 Hz,H7-benzothiazole), 9.90(1H,s,CHO).

Synthesis Example 6

Synthesis of 4-[1-(1-methyl-2-benzimidazolyl)-methoxy]benzaldehyde

The title compound was obtained from 2-chloromethyl-1-methylbenzimidazole in a similar manner as in Synthesis Example 1.

Melting point: 140–142° C.

$^1$H-NMR(CDCl$_3$)δ(ppm): 5.48(2H,s,CH$_2$O), 7.14–7.42 (5H,m,Ar-H), 7.71–7.90(3H,m,Ar-H), 9.88(1H,s,CHO).

Synthesis Example 7

Synthesis of 4-[1-(1-ethoxyethyl-2-benzimidazolyl)-methoxy]benzaldehyde

The title compound was obtained from 2-chloromethyl-1-ethoxyethylbenzimidazole in a similar manner as in Synthesis Example 1.

Melting point: 96–97° C.

$^1$H-NMR(CDCl$_3$)δ(ppm): 1.10(3H,t,J=6.8 Hz,OCH$_2$CH$_3$), 3.29(2H,q,J=6.8 Hz,OCH$_2$CH$_3$), 3.75(2H,t, J=5.4 Hz,NCH$_2$CH$_2$O), 4.49(2H,t,J=5.4 Hz,NCH$_2$CH$_2$O), 5.57(2H,s,CH$_2$O), 7.14–7.47(5H,m,Ar-H), 7.74–7.89(3H, m,Ar-H), 9.89(1H,s,CHO).

Synthesis Example 8

Synthesis of 3-benzyloxybenzaldehyde

The title compound was obtained from benzyl bromide in a similar manner as in Synthesis Example 1.

Melting point: 50.8–52.2° C.

$^1$H-NMR(CDCl$_3$)δ(ppm): 5.11(2H,s,CH$_2$O), 7.21–7.47 (10H,m,Ar-H), 9.96(1H,s,CHO).

Synthesis Example 9

Synthesis of 4-benzyloxybenzaldehyde

The title compound was obtained from benzyl bromide in a similar manner as in Synthesis Example 1.

Melting point: 70.0–71.8° C.

$^1$H-NMR(CDCl$_3$)δ(ppm): 5.14(2H,s,CH$_2$O), 7.05(2H,d, J=8.8 Hz,H3,H5), 7.33–7.45(5H,m,Ph), 7.83(2H,d,J=8.8 Hz,H2,H6), 9.87(1H,s,CHO).

Synthesis Example 10

Synthesis of 3-(2-naphthylmethoxy)benzaldehyde

The title compound was obtained from 2-chloromethylnaphthalene in a similar manner as in Synthesis Example 1.

Melting point: 107–110° C.

$^1$H-NMR(CDCl$_3$)δ(ppm): 5.29(2H,s,CH$_2$O), 7.22–7.32 (1H,m,Ar-H), 7.41–7.59(6H,m,Ar-H), 7.80–7.92(4H,m,Ar-H), 9.98(1H,s,CHO)

Synthesis Example 11

Synthesis of 4-(2-naphthylmethoxy)benzaldehyde

The title compound was obtained from 2-chloromethylnaphthalene in a similar manner as in synthesis Example 1.

Melting point: 106–108° C.

$^1$H-NMR(CDCl$_3$)δ(ppm): 5.31(2H,s,CH$_2$O), 7.12(2H,d, J=8.8 Hz,H3,H5), 7.42–7.58(3H,m,Ar-H), 7.76–7.92(6H,m, Ar-H), 9.89(1H,s,CHO).

Synthesis Example 12

Synthesis of 4-[2-(2-quinolyl)ethenyl]benzaldehyde 1,4-Benzenedialdehyde (30 g, 0.22 mol), 2-methylquinoline (21 g, 0.15 mol) and acetic anhydride (41.5 ml, 0.40 mol) were dissolved in 160 ml of xylene, followed by heating under reflux for 7 hours. After the reaction mixture was allowed to cool down to room temperature, 200 ml of petroleum ether were added and the resulting precipitate was collected by filtration. Further, the mother liquor was concentrated under reduced pressure and the residue was recrystallized from diethyl ether, whereby 13.6 g of the title compound were obtained (yield: 35%).

Melting point: 111.9–113.0° C.

$^1$H-NMR(CDCl$_3$)δ(ppm): 7.46–7.51(2H,m,Ar-H), 7.54–7.80(6H,m,Ar-H,H-olefin), 7.87–7.91 (2H,m,Ar-H), 8.08(1H,d,J=8.4 Hz,Ar-H), 8.14(1H,d,J=8.6 Hz,H4-guinoline), 10.00(1H,s,CHO).

Synthesis Example 13

Synthesis of 4-[2-(7-chloro-2-quinolyl)ethenyl]-benzaldehyde

The title compound was obtained from 7-chloro-2-methylquinoline in a similar manner as in Synthesis Example 12.

Melting point: 178–180° C.

Synthesis Example 14

Synthesis of 3-[2-(2-quinolyl)ethenyl]benzaldehyde

The title compound was obtained from 2-methylquinoline in a similar manner as in Synthesis Example 12.

Melting point: 78.6–80.8° C.

$^1$H-NMR (CDCl$_3$) δ(ppm): 7.42–7.89(9H,m,Ar-H,H-olefin), 8.05–8.16(3H,m,Ar-H), 10.04(1H,s,CHO).

Synthesis Example 15

Synthesis of 2-hydroxy-5-(5-tetrazolyl) acetophenone

A mixture of 2.0 g (12.4 mmol) of 5-cyano-2-hydroxyacetophenone, 4.1 g (62 mmol) of sodium azide and 3.35 g (62 mmol) of ammonium chloride was dissolved in 35 ml of DMF, followed by heating at 100° C. for 3 days. The reaction mixture was poured into water. The resulting mixture was adjusted to pH 5 and was then extracted with ethyl acetate. After the organic layer was dried over Na$_2$SO$_4$, the solvent was distilled off under reduced pressure. The residue was recrystallized form ethanol, whereby 1.42 g of the title compound were obtained (yield: 56%).

Melting point: 181.8–184.9° C.

$^1$H-NMR(DMSO)δ(ppm): 2.69(3H,s,COCH$_3$), 7.20(1H, d,J=8.7 Hz,H3), 8.14(1H,dd,J=1.7,8.7 Hz,H4), 8.52(1H,d,J= 1.7 Hz,H6), 12.07(1H,brs,ArOH).

Synthesis Example 16

Synthesis of 5-bromo-3-carboxy-2-hydroxyacetophenone

1) Concentrated sulfuric acid (0.5 ml) was added under stirring to a mixture of 100 g (0.46 mol) of 5-bromosalicylic acid and 105 ml of acetic anhydride. Several minutes later, 1,000 ml of water were added, and the resulting precipitate was collected by filtration and then washed with water. A white matter, which had been collected by filtration, was dissolved in 1,000 ml of ethyl acetate. The resulting solution was washed with a saturated aqueous solution of sodium chloride (2×300 ml) and was then dried over Na$_2$SO$_4$. The solvent was distilled off under reduced pressure, whereby 105 g of 2-acetyloxy-5-bromobenzoic acid were obtained as white crystals (yield: 88%).

Melting point: 199–203° C.

$^1$H-NMR(DMSO)δ(ppm): 2.26(3H,s,CH$_3$CO$_2$Ar), 7.20 (1H,d,J=8.6 Hz,H3), 7.84(1H,dd,J=2.6,8.6 Hz,H4), 8.03 (1H,d,J=2.6 Hz,H6).

2) A mixture of 100 g (0.39 mol) of 2-acetyloxy-5-bromobenzoic acid and 159 g (1.20 mol) of aluminum chloride was placed in a three-necked flask and was then heated to 160° C. with stirring by a mechanical stirrer. Three hours later, the reaction mixture was allowed to cool down to room temperature. The reaction mixture was then poured into 800 g of ice water which contained 200 ml of concentrated hydrochloric acid. The resulting slurry was extracted with ethyl acetate (3×350 ml). After the extract was washed with 1N hydrochloric acid (3×200 ml) and a saturated aqueous solution of sodium chloride (400 ml), the extract was dried over Na$_2$SO$_4$ and the solvent was then distilled off under reduced pressure. The residue was washed with dichloromethane to remove byproducts, and was then collected by filtration, whereby 36.4 g of the title compound were obtained as brown powder (yield: 36%).

Melting point: 200.1° C.

$^1$H-NMR(DMSO)δ(ppm): 2.59(3H,s,CH$_3$CO), 7.92(1H, d,J=2.7 Hz,H4), 8.01(1H,d,J=2.7 Hz,H6), 11.64(1H,brs, ArOH,ArCO$_2$H).

Synthesis Example 17

Synthesis of 3-carboxy-5-chloro-2-hydroxy-acetophenone

The title compound was obtained in a similar manner as in Synthesis Example 16.

Melting point: 173.7–175.8° C.

$^1$H-NMR(DMSO)δ(ppm): 2.60(3H,s,COCH$_3$), 7.84(1H, d,J=2.7 Hz,H6), 7.92(1H,d,J=2.7 Hz,H4), 12.28(2H,brs, ArOH,ArCO$_2$H).

Synthesis Example 18

Synthesis of 3-carboxy-5-fluoro-2-hydroxy-acetophenone

The title compound was obtained in a similar manner as in Synthesis Example 16.

Melting point: 156.8–159.2° C.

$^1$H-NMR(DMSO)δ(ppm): 2.61(3H,s,COCH$_3$), 7.66–7.79 (2H,m,H3,H5), 11.88(2H,brs,ArOH,ArCO$_2$H).

Synthesis Example 19

Synthesis of 3-carboxy-2-hydroxy-5-methylacetophenone

The title compound was obtained in a similar manner as in Synthesis Example 16.

Melting point: 122.2–125.8° C.

$^1$H-NMR(DMSO)δ(ppm): 2.32(3H,s,ArCH$_3$), 2.67(3H,s, COCH$_3$), 7.77(1H,d,J=2.3 Hz,H3/5), 8.05(1H,d,J=2.3 Hz,H3/5), 9.25(1H,brs,CO$_2$H), 13.45(1H,brs,ArOH).

Synthesis Example 20

Synthesis of 3-carboxy-2-hydroxyacetophenone

5-Bromo-3-carboxy-2-hydroxyacetophenone (10.0 g, 38.6 mmol) was dissolved in 75 ml of ethanol, followed by the addition of 1.0 g of 10% Pd/C. Under a hydrogen gas stream, catalytic reduction was conducted at room temperature for 2 hours. The catalyst was filtered off, and the filtrate was neutralized with 2N NaOH. After the solvent was distilled off, a white matter as a residue was dissolved in 1N NaOH, followed by the addition of 3N HCl. The resulting precipitate was collected by filtration, whereby 6.8 g of the title compound were obtained as a white solid (yield: 98%).

Melting point: 131.8–133.0° C.

$^1$H-NMR (DMSO) δ(ppm): 2.63(3H,s,$CH_3$CoAr), 7.03 (1H,t,J=7.8 Hz,H5), 7.94(1H,dd,J=1.8,7.8 Hz,H4), 8.03(1H, dd,J=1.8,7.8 Hz,H6).

Synthesis Example 21

Synthesis of 5-t-butyl-3-ethoxycarbonyl-2-hydroxyacetophenone

Ethyl salicylate (10 g, 60 mmol) was dissolved in 50 ml of dichloromethane, followed by the addition of 11.75 g (88 mmol) of anhydrous aluminum chloride. Then, 5.6 g (60 mmol) of t-butyl chloride were dropped. After the resultant mixture was stirred at room temperature for 3 hours, 14.8 g (120 mmol) of acetyl bromide were added slowly. Subsequent to overnight stirring, the reaction mixture was poured into ice water which contained 3 M hydrochloric acid. The resulting mixture was extracted with ethyl acetate, the solvent was distilled off under reduced pressure, and the residue was purified by column chromatography (ethyl acetate/petroleum ether=1/20), whereby 7.20 g of the title compound were obtained (yield: 45%).

Melting point: 63.5–65.3° C.

$^1$H-NMR($CDCl_3$)δ(ppm): 1.24(9H,s,C($CH_3$)$_3$), 1.36(3H, t,J=7.1 Hz,$CO_2CH_2CH_3$), 2.62(3H,s,$COCH_3$), 4.36(2H,q,J= 7.1 Hz,$Co_2CH_2CH_3$), 7.93(1H,d,J=2.7 Hz,H4), 7.98(1H,d, J=2.7 Hz,H6).

Synthesis Example 22

Synthesis of 3-cyano-5-chloro-2-hydroxyacetophenone

2-Amino-4-chlorophenol (50 g, 0.35 mol) was dissolved in 500 ml of 2.5N HCl. The resulting solution was cooled to 0° C., at which a solution of 25.25 g (0.37 mol) of sodium nitrite in 50 ml of water was added slowly. After stirring for 30 minutes, a chilled solution of 70 g (0.42 mol) of potassium iodide in 100 ml of water was added slowly. The temperature of the reaction mixture was allowed to rise to room temperature, at which the reaction mixture was stirred overnight. The reaction mixture was extracted with ethyl acetate and the solvent was distilled off under reduced pressure, whereby 89.7 g of 4-chloro-2-iodophenol were obtained (yield: 99%). Next, 85 g (0.33 mol) of the 4-chloro-2-iodophenol and 32.5 g (0.36 mol) of copper cyanide were dissolved in 150 ml of DMF. After the resultant solution was heated under reflux for 2 hours, the DMF was distilled off under reduced pressure. The residue was extracted with ethyl acetate and the extract was then washed with water. An insoluble matter was filtered off. The solvent was then distilled off under reduced pressure, whereby 40.4 g of 5-chloro-2-hydroxybenzonitrile were obtained (yield: 80%) (melting point: 150.3–152.6° C.).

Further, 39.25 g (0.25 mol) of the 5-chloro-2-hydroxybenzonitrile were dissolved in 40 ml of acetic anhydride, followed by the addition of 0.5 ml of concentrated sulfuric acid. After the reaction mixture was heated at 60° C. for 10 minutes, water was added to the reaction mixture, followed by extraction with ethyl acetate. The organic layer was washed with 1N NaOH and a saturated aqueous solution of sodium chloride and was then dried over $Na_2SO_4$. The solvent was distilled off under reduced pressure, whereby 45 g of 2-acetoxy-5-chlorobenzonitrile (yield: 92%). A mixture of 44 g of the 2-acetoxy-5-chlorobenzonitrile and 99 g (0.75 mol) of aluminum chloride was then heated at 160° C. for 3 hours. The reaction mixture was allowed to cool down to room temperature, and was then poured into ice water which contained 100 ml of concentrated hydrochloric acid. The slurry was extracted with ethyl acetate (3×350 ml). The extract was washed with 1N hydrochloric acid (3×200 ml) and a saturated aqueous solution of sodium chloride (400 ml) and was then dried over $Na_2SO_4$. The solvent was distilled off under reduced pressure. The residue was washed with dichloromethane to remove byproducts, and was then collected by filtration, whereby 16.5 g of the title compound were obtained as brown powder (yield: 38%).

Melting point: 137.9–139.8° C.

$^1$H-NMR($CDCl_3$)δ(ppm): 2.72(3H,s,$COCH_3$), 8.21(1H,d, J=2.5 Hz,H4/6), 8.32(1H,d,J=2.5 Hz,H4/6), 12.77(1H,brs, ArOH).

Synthesis Example 23

Synthesis of 5-chloro-2-hydroxy-3-(5-tetrazolyl)-acetophenone

The title compound was obtained in a similar manner as in Synthesis Example 15.

$^1$H-NMR (DMSO)δ(ppm): 2.76(3H,s,$COCH_3$), 8.26(2H, s,J=2.5 Hz,H4,H6).

Synthesis Example 24

Synthesis of methyl 3-acetyl-4-methoxybenzoate

3-Acetyl-4-hydroxybenzoic acid (3.60 g, 20 mmol) and methyl iodide (5.68 g, 40 mmol) were dissolved in 60 ml of DMF, followed by the addition of 11.06 g (80 mmol) of potassium carbonate. The resulting mixture was stirred at room temperature for 2 hours. The DMF was distilled off under reduced pressure, followed by the addition of water. The resulting mixture was extracted with chloroform. The organic layer was dried over $MgSO_4$, the solvent was distilled off under reduced pressure, and the residue was recrystallized from acetone-hexane, whereby 1.42 g of the title compound were obtained as brown powder (yield: 34%).

Melting point: 83–85° C.

$^1$H-NMR($CDCl_3$)δ(ppm): 2.62(3H,s,$COCH_3$), 3.90(3H,s, $CO_2CH_3$), 3.98(3H,s,$OCH_3$), 7.02(1H,d,J=8.8 Hz,H5), 8.16 (1H,dd,J=2.0,8.8 Hz,H6). 8.40(1H,d,J=2.0 Hz,H2).

Synthesis Example 25

Synthesis of 3-acetyl-5-chloro-4-hydroxybenzoic Acid

3-Chloro-4-hydroxybenzoic acid hemihydrate (10.16 g, 56 mmol) was dissolved in 20 ml of acetic anhydride, followed by the addition of 0.5 ml of concentrated sulfuric acid. The resulting mixture was stirred at 100° C. for 3 hours and was then allowed to stand overnight at room temperature. The precipitate was collected by filtration and then washed with benzene, whereby 8.95 g of 4-acetoxy-3-chlorobenzoic acid were obtained (yield: 75%, melting point: 149–151° C.). A mixture of 8.95 g (41.7 mmol) of 4-acetoxy-3-chlorobenzoic acid and 22.23 g (167 mmol) of aluminum chloride was then heated at 180° C. for 3 hours. Subsequent to the addition of ice and 1N hydrochloric acid, the resultant mixture was extracted with ethyl acetate. The organic layer was washed with water and was then dried over $MgSO_4$. The solvent was distilled off under reduced pressure and the residue was recrystallized from ethyl acetate, whereby 2.97 g of the title compound were obtained as yellow powder (yield: 33%).

Melting point: 238–241° C.

$^1$H-NMR($CD_3OD$)δ(ppm): 2.73(3H,s,$COCH_3$), 8.17(1H, d,J=2.0 Hz,H2/6), 8.48(1H,d,J=2.0 Hz,H2/6).

Synthesis Example 26

Synthesis of 4-acetyl-3-hydroxybenzoic Acid

Concentrated sulfuric acid (0.2 ml) was added to a solution of 10.07 g (72.9 mol) of 3-hydroxybenzoic acid in 10 ml of acetic anhydride. The resulting mixture was stirred at 60° C. for 1 hour and was then allowed to stand overnight at room temperature. The resulting precipitate was collected by filtration, washed with benzene, and then dried in air. The precipitate was recrystallized from acetone-hexane, whereby 8.92 g of 3-acetoxybenzoic acid were obtained as colorless prisms (yield: 67.9%, melting point: 149–151° C.). A mixture of 8.92 g (49.5 mmol) of 3-acetoxybenzoic acid and 26.33 g (198 mmol) of aluminum chloride was then heated at 160° C. for 3 hours. Subsequent to the addition of ice and 1N hydrochloric acid, the resulting mixture was extracted with ethyl acetate. The organic layer was washed with a saturated aqueous solution of sodium chloride and was then dried over $MgSO_4$. The solvent was distilled off under reduced pressure. The residue was recrystallized from ethanol, whereby 1.61 g of the title compound were obtained as pale yellow powder (yield: 18%).

Melting point: 204–205° C.

$^1$H-NMR($CDCl_3$-DMSO)δ(ppm): 2.70(3H,s,$COCH_3$), 7.52(1H,dd,J=2.0,8.8 Hz,H6), 7.54(1H,d,J=2.0 Hz,H2), 7.87 (1H,d,J=8.8 Hz,H5), 12.07(1H,s,OH).

Synthesis Example 27

Synthesis of n-butyl 3-acetyl-4-butoxybenzoate

The title compound was obtained in a similar manner as in Synthesis Example 24

Melting point: 39–40° C.

$^1$H-NMR($CDCl_3$)δ(ppm): 0.97(3H,t,J=6.8 Hz,$CH_2CH_2CH_2C\underline{H}_3$), 1.01(3H,t,J=6.8 Hz,$CH_2CH_2CH_2C\underline{H}_3$), 1.35–1.96(8H,m,$OCH_2C\underline{H}_2C\underline{H}_2CH_3,CO_2CH_2C\underline{H}_2C\underline{H}_2CH_3$), 2.64(3H,s,$COCH_3$), 4.13(2H,t,J=6.8 Hz,$CO_2C\underline{H}_2CH_2CH_2CH_3$), 4.30(2H,t,J=6.8 Hz,$OC\underline{H}_2CH_2CH_2CH_3$), 6.99(1H,d,J=8.8 Hz,H5), 8.13(1H,dd,J-2.5,8.8 Hz,H6), 8.39 (1H,d,J=2.5 Hz,H2).

Synthesis Example 28

Synthesis of 3-[1-(1-ethoxyethylbenzimidazol-2-yl) methoxy]benzaldehyde

The title compound was obtained in a similar manner as in Synthesis Example 1.

Melting point: 98–100° C.

$^1$H-NMR($CDCl_3$)δ(ppm): 1.10(3H,t,J=6.8 Hz,$OCH_2C\underline{H}_3$), 3.39(2H,q,J=6.8 Hz,$OC\underline{H}_2CH_3$), 3.76(2H,t,J=5.4 Hz,$NCH_2C\underline{H}_2$), 4.49(2H,t,J=5.4 Hz,$NC\underline{H}_2CH_2$), 5.52(2H,s, $CH_2O$), 7.23–7.53(6H,m,Ar-H), 7.58(1H,d,J=1.0 Hz,Ar-H), 7.74–7.83(1H,m,Ar-H), 9.98(1H,s,CHO).

Synthesis Example 29

Synthesis of 3-acetyl-4-hydroxy-5-methylbenzoic Acid

1) A mixed solution of 10.89 g (58 mmol) of 4-bromo-cresol and 10.39 g (116 mmol) of copper cyanide in 50 ml of NMP was stirred at 190° C. for 2 hours, followed by the addition of 43 g of $FeCl_3.6H_2O$, 65 ml of water and 11 ml of concentrated hydrochloric acid. The resulting mixture was stirred at 80° C. for 30 minutes and was then allowed to cool down. Water and ethyl acetate were added to the reaction mixture, followed by separation into a water layer and an organic layer. The organic layer was dried over $Na_2SO_4$, and the solvent was then distilled off under reduced pressure. The residue as purified by column chromatography (chloroform/methanol=40/1), whereby 10.32 g of 4-cyanocresol were obtained as a dark brown oil.

2) 50% sodium hydroxide (80 ml) was added to a solution of 10.32 g of the 4-cyanocresol in 100 ml of ethanol, followed by overnight heating under reflux. Concentrated hydrochloric acid was added to acidify the reaction mixture. Crystals so precipitated were collected by filtration, washed with water and then dried, whereby 5.91 g of 4-hydroxy-3-methylbenzoic acid were obtained as white powder (yield: 66.9%).

Melting point: 164–165° C.

$^1$H-NMR($CDCl_3$)δ(ppm): 2.16(3H,s,$CH_3$), 6.81(1H,d,J= 8.3 Hz,H6), 7.60(1H,dd,J=2.0,8.1 Hz,H5), 7.66(1H,d,J=1.2 Hz,H3), 9.47(1H,br.s,COOH).

3) A solution of 5.42 g (35.6 mmol) of the 4-hydroxy-3-methylbenzoic acid in 50 ml of pyridine was added to 16.8 ml (178 mmol) of acetic anhydride. The resulting mixture was stirred overnight at room temperature, and the reaction mixture was distilled off under reduced pressure. The residue was dissolved in ethyl acetate. The resulting solution was washed with 2N hydrochloric acid and a saturated aqueous solution of sodium chloride and was then dried over $Na_2SO_4$. The solvent was distilled off under reduced pressure. The residue was recrystallized from ethyl acetate-hexane, whereby 3.64 g of 4-acetoxy-3-methylbenzoic acid were obtained as white powder (yield: 52.6%).

Melting point: 153° C.

$^1$H-NMR($CDCl_3$)δ(ppm): 2.25(3H,s,C5-$CH_3$), 2.36(3H,s, $CH_3COO$), 7.13(1H,d,J=8.3 Hz,H3), 7.97(1H,ddd,J=0.7, 1.7,8.3 Hz,H2), 8.01(1H,dd,J=0.7,1.7 Hz,H6).

4) A mixture of 3.01 g (15.5 mmol) of the 4-acetoxy-3-methylbenzoic acid and 8.27 g (62 mmol) of aluminum chloride was gradually heated to 160° C. Three hours later, the reaction mixture was poured into ice water, and precipitated crystals were extracted with ethyl acetate. The organic layer was washed with water and then dried over $Na_2SO_4$. The solvent was distilled off under reduced pressure and the residue was recrystallized from ethyl acetate-hexane, whereby 1.78 g of the title compound were obtained as brown powder (yield: 59.3%).

Melting point: 215–218° C.

$^1$H-NMR(DMSO-$d_6$)δ(ppm): 2.23(3H,t,J=0.7 Hz,C5-$CH_3$), 2.67(3H,s,$CH_3CO$), 7.95(1H,td,J=0.7,2.2 Hz,H6), 8.30(1H,dd,J=0.7,2.2 Hz,H2).

EXAMPLE 1

Synthesis of 5'-carboxy-2'-hydroxy-4-[(2-quinolyl)-methoxy]chalcone

A mixture of 2.63 g (10 mmol) of 4-(2-quinolyl-methoxy) benzaldehyde and 1.80 g (10 mmol) of 5-carboxy-2- hydroxyacetophenone was dissolved in 50 ml of ethanol, followed by the addition of 25 ml of a 25% aqueous solution of KOH. The resulting mixture was stirred at room temperature for 1 week. The reaction mixture was poured into ice water, followed by acidification with 3N HCl. A precipitate was collected by filtration, washed with water and then recrystallized from ethanol-DMF, whereby 1.28 g of the title compound were obtained as yellow powder (yield: 30%).

Melting point: 242.7–246.7° C.

$^1$H-NMR(DMSO)δ(ppm): 5.47(2H,s,CH$_2$O), 7.10(1H,d, J=8.7 Hz,H3'), 7.16(2H,d,J=8.8 Hz,H3,H5), 7.61–7.65(1H, m,H6-quinoline), 7.69(1H,d,J=8.5 Hz,H3-quinoline), 7.77 (1H,d,J=15.6 Hz,Hα), 7.77–7.82(1H,m,H7-quinoline), 7.81 (1H,d,J=15.6 Hz,Hβ), 7.88(2H,d,J=8.8 Hz,H2,H6), 8.00 (1H,d,J=8.2 Hz,5H-quinoline), 8.03–8.05(2H,m,H4',H8-quinoline), 8.43(1H,d,J=8.5 Hz,H4-quinoline), 8.55(1H,d, J=2.1 Hz,H6').

The compounds shown below in Table 1 were obtained in a similar manner as in Example 1.

TABLE 1

| Ex. | Compound Name | m.p. (° C.) |
|---|---|---|
| 2 | 5'-Carboxy-2'-hydroxy-3-[(2-quinolyl)methoxy]chalcone | 190.6–192.4 |
| 3 | 5'-Carboxy-2'-hydroxy-2-[(2-quinolyl)methoxy]chalcone | 168.9–169.1 |
| 4 | 4-Benzyloxy-5'-carboxy-2'-hydroxychalcone | 212.1–215.3 |
| 5 | 3-Benzyloxy-5'-carboxy-2'-hydroxychalcone | 103.4–104.9 |
| 6 | 2-Benzyloxy-5'-carboxy-2'-hydroxychalcone | 172.1–175.5 |
| 7 | 3'-Carboxy-2'-hydroxy-4-[(2-quinolyl)methoxy]chalcone | 232.9–235.3 |
| 8 | 3'-Carboxy-5'-fluoro-2'-hydroxy-4-[(2-quinolyl)methoxy]chalcone | 219.5–220.3 |
| 9 | 3'-Carboxy-5'-chloro-2'-hydroxy-4-[(2-quinolyl)methoxy]chalcone | 222.1–222.5 |
| 10 | 3'-Carboxy-5'-chloro-2'-hydroxy-3-[(2-quinolyl)methoxy]chalcone | 175–177(d) |
| 11 | 5'-Bromo-3'-carboxy-2'-hydroxy-4-[(2-quinolyl)methoxy]chalcone | 233.7–234.2 |
| 12 | 4'-Carboxy-2'-hydroxy-4-[(2-quinolyl)methoxy]chalcone | 228–231(d) |
| 13 | 4'-Carboxy-2'-hydroxy-3-E(2 quinolyl)methoxy]chalcone | 233–234(d) |
| 14 | 4'-Carboxy-4-[1-(1-ethoxyethyl-benzimidazol-2-yl)methoxy]-2'-hydroxychalcone | 222–225(d) |
| 15 | 2'-Carboxy-4-[(2-quinolyl)-methoxy]chalcone | 238–240(d) |
| 16 | 2'-Carboxy-3-[(2-quinolyl)-methoxy]chalcone | 131–134 |

EXAMPLE 17

Synthesis of 5'-ethoxycarbonyl-2'-hydroxy-4-[(2-quinolyl)chalcone

A mixture of 0.527 g (2 mmol) of 4-(2-quinolyl-methoxy) benzaldehyde and 0.416 g (2 mmol) of 5-ethoxyl-2-hydroxyacetophenone was dissolved in a 7% solution of KOH in ethanol (25 ml), followed by stirring at room temperature for 1 week. The reaction mixture was poured into ice water, followed by acidification with 3N HCl. A precipitate was collected by filtration, washed with water and then recrystallized from ethanol-DMF, whereby 0.499 g of the title compound was obtained (yield: 55%).

Melting point: 167.7–168.1° C.

$^1$H-NMR(CDCl$_3$)δ(ppm): 4.41(2H,q,J=7.1 Hz,CO$_2$CH$_2$CH$_3$), 5.46(2H,s,CH$_2$O), 7.04(1H,d,J=8.7 Hz,H3'), 7.11(2H,d,J=8.7 Hz,H5), 7.41(3H,t,J=7.1 Hz,CO$_2$CH$_2$CH$_3$), 7.56–7.59(1H,m,H6-quinoline), 7.60 (1H,d,J=15.3 Hz,Hα), 7.66–7.68(1H,m,H7-quinoline), 7.67 (2H,d,J=8.7 Hz,H2,H6), 7.74–7.78(1H,d,m,H5-quinoline), 7.84(1H,d,J=8.1 Hz,H8-quinoline), 7.94(1H,d,J=15.3 Hz,Hβ), 8.10(1H,d,J=8.5 Hz,H3-quinoline), 8.15(1H,dd,J= 2.0,8.7 Hz,H4'), 8.22(1H,d,J=8.5 Hz,H4-quinoline), 8.65 (1H,d,J=2.0 Hz,H6'), 13.44(1H,s,ArOH).

The compounds shown below in Table 2 and Table 3 were obtained in a similar manner as in Example 17.

TABLE 2

| Ex. | Compound Name | m.p. (° C.) |
|---|---|---|
| 18 | 5'-Cyano-2'-hydroxy-4-[(2-quinolyl) methoxy]chalcone | 192.6–193.8 |
| 19 | 2'-Hydroxy-4-[(2-quinolyl)-methoxy]-5'-(5-tetrazolyl)-chalcone | 232.7–233.3 |
| 20 | 2'-Hydroxy-3-[(2-quinolyl)-methoxy]-5'-(5-tetrazolyl)-chalcone | 228.4–229.9 |
| 21 | 5'-Carboxy-3'-chloro-2'-hydroxy-4-[(2-quinolyl)IrLethoxy]chalcone | 234–245(d) |
| 22 | 2'-Hydroxy-4-[1-(1-methyl-2-benzimidazolyl)methoxy]-5'-(5-tetrazolyl)chalcone | 248–250 |
| 23 | 4-[1-(1-Ethoxyethyl-2-benzimidazolyl)inethoxy]-2'-hydroxy-5'-(5-tetrazolyl)chalcone | 234–236(d) |
| 24 | 4-[1-(2-Benzothiazolyl)methoxy]-2'-hydroxy-5'-(5-tetrazolyl)-chalcone | 244–247(d) |
| 25 | 2'-Hydroxy-3-(2-naphthyl-methoxy)-5'-(5-tetrazolyl)-chalcone | 217–218(d) |
| 26 | 2'-Hydroxy-4-(2-naphthyl-methoxy)-5'-(5-tetrazolyl)-chalcone | 256–258(d) |
| 27 | 4-[(7-Chloro-2-quinolyl)methoxy]-2'-hydroxy-5'-(5-tetrazolyl)-chalcone | 173–177(d) |
| 28 | 4-[2-(7-Chloro-2-quinolyl)-ethenyl]-2'-hydroxy-5'-(5-tetrazolyl)chalcone | 262–265(d) |
| 29 | 5'-Carboxy-2'-methoxy-4-[(2-quinolyl)methoxy]chalcone | 224–226(d) |

TABLE 3

| Ex. | Compound Name | m.p. (° C.) |
|---|---|---|
| 30 | 5'-Carboxy-2'-methoxy-3-(2-quinolylmethoxy)chalcone.HCl | 228–231(d) |
| 31 | 2'-n-Butoxy-5'-carboxy-3-(2-quinolylmethoxy)chalcone | 170–173(d) |
| 32 | 2'-n-Butoxy-5'-carboxy-4-(2-quinolylmethoxy)chalcone.HCl | 232–235(d) |
| 33 | 3-[(1-Ethoxyethylbenziinidazol-2-yl)methoxy]-2'-hydroxy-5'-(tetrazol-5-yl)chalcone.HCl | 234–236(d) |
| 34 | 3'-Carboxy-5'-chloro-3-(1-ethoxyethylbenzimidazol-2-yl)-methoxy]-2'-hydroxychalcone | 206–208(d) |
| 35 | 3'-cyano-4-(2-quinolylmethoxy)-chalcone | 172–175 |
| 36 | 3'-Cyano-3-(2-quinolylmethoxy)-chalcone | 175–177 |
| 37 | 4'-Carboxy-3-[(1-ethoxyethyl-benzimidazol-2-yl)methoxy]-2'-hydroxychalcone.HCl | 217–220(d) |
| 38 | 5'-Carboxy-2'-hydroxy-3'-methyl-3-(2-quinolylmethoxy)chalcone | 195–198(d) |
| 39 | 5'-Carboxy-2'-hydroxy-3'-methyl-4-(2-quinolylmethoxy)chalcone | 246–248(d) |

EXAMPLE 40

Synthesis of 3'-carboxy-2'-hydroxy-3-[(2-quinolyl)-ethenyl]chalcone

A mixture of 1.30 g (5 mmol) of 4-[2-(2-quinolyl)ethenyl] benzaldehyde and 0.90 g (5 mmol) of 3-carboxy-2-hydroxyacetophenone was dissolved in 50 ml of THF and 50 ml of ethanol, followed by the addition of 30 ml of a 25% aqueous solution of KOH. The resulting mixture was stirred at room temperature for 1 to 2 weeks. Whenever a precipitate was formed in the course of the stirring, the solvent was added. The reaction mixture was poured into ice water, followed by acidification with 3N HCl. A precipitate was collected by filtration and was then purified by column chromatography and recrystallization, whereby 0.70 g of the title compound was obtained as (yield: 33%).

Melting point: 237.2–240.2° C.

$^1$H-NMR(DMSO)δ(ppm):

5.44(2H,s,CH$_2$O), 7.06(1H,t,J=7.7 Hz,H5'), 7.15–7.18 (1H,m,H4), 7.37–7.38(2H,m,H5,H6), 7.55(1H,s,H2), 7.60–7.62(1H,m,H6-quinoline), 7.64–7.67(2H,m,Hα,Hβ), 7.72(1H,d,J=8.5 Hz,H3-quinoline), 7.76–7.80(1H,m,H7-quinoline), 7.92–7.94(1H,m,H4'/H6'), 7.95–8.02(3H,m,H4'/H6',H5-quinoline,H8-quinoline), 8.43(1H,d,J=8.5 Hz,H4-quinoline).

The compounds shown below in Table 4 were obtained in a similar manner as in Example 40.

TABLE 4

| Ex. | Compound Name | m.p. (° C.) |
|---|---|---|
| 41 | 3'-Carboxy-2'-hydroxy-3-[(2-quinolyl)methoxy]chalcone | 176.9–178.1 |
| 42 | 5'-Bromo-3'-carboxy-2'-hydroxy-3-[(2-quinolyl)methoxy]chalcone | 185.1–186.0 |
| 43 | 3'-Carboxy-2'-hydroxy-4-[2-(2-quinolyl)ethenyl]chalcone | 267.1–269.2 |
| 44 | 5'-Carboxy-2'-hydroxy-4-[2-(2-quinolyl)ethenyl]chalcone | 257.7–260.0 |
| 45 | 5'-Cyano-2'-hydroxy-3-[2-(2-quinolyl)ethenyl]chalcone | 221.6–222.3 |
| 46 | 2'-Hydroxy-3-[2-(2-quinolyl)-ethenyl]-5'-(5-tetrazolyl)-chalcone | 226.0–228.2 |
| 47 | 4-Benzyloxy-5'-ethoxycarbonyl-2'-hydroxychalcone | 133.7–135.9 |
| 48 | 3'-Carboxy-5'-fluoro-2'-hydroxy-3-[2-(2-quinolyl)ethenyl]chalcone | 275.7–277.1 |
| 49 | 3'-Carboxy-5'-chloro-2'-hydroxy-3-[2-(2-quinolyl)ethenyl]chalcone | 278.5–280.9 |
| 50 | 5'-Bromo-3'-carboxy-2'-hydroxy-3-[2-(2-quinolyl)ethenyl]chalcone | 264.1–266.0 |
| 51 | 3'-Carboxy-2'-hydroxy-5'-methyl-3-[2-(2-quinolyl)ethenyl]chalcone | 163.2–163.7 |
| 52 | 5'-t-Butyl-3'-carboxy-2'-hydroxy-3-[2-(2-quinolyl)ethenyl]chalcone | 234.6–236.7 |
| 53 | 5'-Chloro-3'-cyano-2'-hydroxy-3-[2-(2-quinolyl)ethenyl]chalcone | 231.6–233.3 |
| 54 | 5'-Chloro-2'-hydroxy-3-[2-(2-quinolyl)ethenyl]-3'-(5-tetrazolyl)chalcone | >300 |
| 55 | 5'-(Carboxymethoxy)-2'-hydroxy-3-[2-(2-quinolyl)ethenyl]chalcone | 220.0–220.9 |
| 56 | 2'-Hydroxy-3-[2-(2-quinolyl)-ethenyl]-5'-[(5-tetrazolyl)-methoxy]chalcone | >300 |
| 57 | 4'-(Carboxymethoxy)-2'-hydroxy-3-[2-(2-quinolyl)ethenyl]chalcone | >300 |
| 58 | 5'-Cyano-2'-hydroxy-3-[(2-quinolyl)methoxy]chalcone | 210.4–211.9 |
| 59 | 5'-Chloro-2'-hydroxy-4-[2-(2-quinolyl)ethenyl]-3'-(5-tetrazolyl)chalcone | >300 |

Test 1

Antileukotriene D$_4$ Action (In vitro Test)

An isolated guinea pig ileum was cut into about 2 cm lengths. Each ileum piece was suspended in a 20-ml organ bath filled with the Krebs buffer. An isotonic contractive response by leukotriene D$_4$ was recorded on a recorder. The Krebs buffer was controlled at 37° C., through which a mixed gas (95%O$_2$-5%CO$_2$) was bubbled. First, leukotriene D$_4$ was added to an organ bath to measure its dose-response. After the ileum piece was washed several times with the buffer, a test compound (will be identified by its example number; this will apply likewise hereinafter) of a predetermined specific concentration was added. Subsequent to incubation for 30 minutes, the dose-response of leukotriene D$_4$ was measured. The results are shown in Table 5.

TABLE 5

| Test comp'd | Anti-LTD$_4$ action (IC$_{50}$ value) |
|---|---|
| 19 | 6.7 × 10$^{-8}$ M |
| 23 | 4.8 × 10$^{-7}$ M |
| 29 | 2.9 × 10$^{-7}$ M |
| 40 | 1.2 × 10$^{-7}$ M |

Test 2

Leukotriene D$_4$ Receptor Binding Inhibition Test 10 mM piperazine N,N-bis(2-ethanesulfonate) buffer (pH 7.5, 0.3 ml) which contained 0.2 nM [$^3$H]leukotriene D$_4$, guinea pig pulmomembranous protein and a test compound was incubated for 30 minutes. An ice-cold tris hydrochloride/sodium chloride buffer (10 mM/100 mM, pH 7.5) was added to terminate the reaction, followed by immediate filtration through a Wattman CF/C filter. The filter was washed twice with 20 ml aliquots of the ice-cold buffer. The radio-activity of the residue was measured by a liquid scintillation counter. From a measurement value obtained without the addition of the test compound and measurements values obtained upon addition of the test compound at various concentrations, the dose-response of the inhibitory action of the test compound was measured and the 50% inhibitory concentration (IC$_{50}$) was determined. Using the Cheng-Prusoff formula, a dissociation constant (K$_D$) was calculated from the IC$_{50}$. From a binding assay, it was found that the maximum binding (Bmax) of 2 μM leukotriene D$_4$ was 988 fmol/mg protein. Further, the dissociation constant (K$_D$) of [$^3$H]leukotriene D$_4$ was 2.616× 10$^{-10}$M and when analyzed by a Hill plot, its slope was found to be 0.99. Incidentally, the values in Table 6 indicate dissociation constants K$_D$ (mol) or inhibition rate (%) at a high concentration (10 μM).

TABLE 6

| Test comp'd | LTD$_4$ receptor (%) |
|---|---|
| 1 | 4.50 × 10$^{-7}$ M |
| 2 | 6.90 × 10$^{-7}$ M |
| 3 | 18% |

TABLE 6-continued

| Test comp'd | LTD$_4$ receptor (%) |
|---|---|
| 4 | 23% |
| 5 | 3.35 × 10$^{-5}$ M |
| 6 | 0% |
| 7 | 3.07 × 10$^{-7}$ M |
| 8 | 3.96 × 10$^{-7}$ M |
| 9 | 7.32 × 10$^{-7}$ M |
| 10 | — |
| 11 | 2.10 × 10$^{-6}$ M |
| 12 | — |
| 13 | — |
| 14 | — |
| 15 | — |
| 16 | — |
| 17 | 16% |
| 18 | 4.31 × 10$^{-6}$ M |
| 19 | 1.41 × 10$^{-8}$ M |
| 20 | 2.09 × 10$^{-7}$ M |
| 21 | 1.70 × 10$^{-6}$ M |
| 22 | 3.18 × 10$^{-8}$ M |
| 23 | 5.27 × 10$^{-7}$ M |
| 24 | 2.33 × 10$^{-7}$ M |
| 25 | 1.92 × 10$^{-5}$ M |
| 26 | 4% |
| 27 | 1.96 × 10$^{-7}$ M |
| 28 | 2.39 × 10$^{-7}$ M |
| 29 | 1.88 × 10$^{-7}$ M |
| 30 | 3.57 × 10$^{-7}$ M |
| 31 | 3.00 × 10$^{-7}$ M |
| 32 | 41% |
| 33 | 8.85 × 10$^{-6}$ M |
| 34 | 1.05 × 10$^{-5}$ M |
| 35 | 8% |
| 36 | 6% |
| 37 | 26% |
| 38 | 2.24 × 10$^{-6}$ M |
| 39 | 1.00 × 10$^{-6}$ M |
| 40 | 2.62 × 10$^{-8}$ M |
| 41 | 4.15 × 10$^{-7}$ M |
| 42 | 2.05 × 10$^{-7}$ M |
| 43 | 2.00 × 10$^{-7}$ M |
| 44 | 5.85 × 10$^{-7}$ M |
| 45 | 3.46 × 10$^{-7}$ M |
| 46 | 2.10 × 10$^{-8}$ M |
| 47 | — |
| 48 | 1.40 × 10$^{-7}$ M |
| 49 | 6.64 × 10$^{-9}$ M |
| 50 | 2.07 × 10$^{-7}$ M |
| 51 | 1.05 × 10$^{-7}$ M |
| 52 | 2.08 × 10$^{-7}$ M |
| 53 | 4.49 × 10$^{-7}$ M |
| 54 | 8.28 × 10$^{-7}$ M |
| 55 | 1.75 × 10$^{-7}$ M |
| 56 | 4.46 × 10$^{-8}$ M |
| 57 | 2.04 × 10$^{-7}$ M |
| 58 | 38% |
| 59 | — |

Capability of Exploitation in Industry

The chalcone derivatives (1) and their salts and solvates, according to the present invention, have excellent cys-LT receptor antagonism, and are therefore useful as drugs for the therapy or prevention of asthma, allergic rhinitis, allergic dermatitis, allergic conjunctivitis, urticaria, psoriasis, rheumatism, inflammatory colitis, cerebral ischemia, cerebral apoplexy and the like.

We claim:

1. A chalcone derivative represented by the following formula (I):

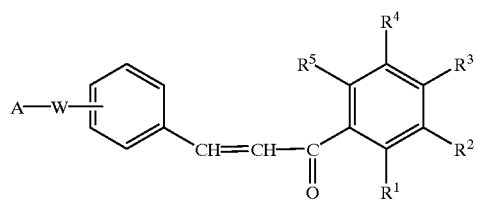

wherein
A represents the group

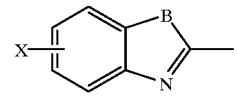

in which
X represents hydrogen, halogen, hydroxyl, lower alkyl or lower alkoxyl and B represents —CH=CH—, —N(R$^6$)—, R$^6$ being a lower alkyl group or a lower alkoxyalkyl group, —O— or —S—,
W represents —CH=CH— or —CH$_2$O —, and
one of groups represented by R$^1$, R$^2$, R$^3$, R$^4$ and R$^5$ represents carboxyl, cyano, alkyloxycarbonyl, tetrazolyl, —CONHR$^7$, in which R$^7$ represents hydrogen or lower alkyl, or —O(CH$_2$)$_n$R$^8$ in which R$^8$ represents carboxyl, alkyloxycarbonyl or tetrazolyl and n stands for a number of from 1 to 4, and the remaining groups of R$^1$ to R$^5$ may be the same or different and each independently represent hydrogen, halogen, hydroxyl, lower alkyl or lower alkoxyl,
with the proviso that a compound in which one of R$^1$ to R$^5$ represents a carboxyl or cyano group and all the remaining groups of R$^1$ to R$^5$ are independently a hydrogen atom is excluded; or
a salt or solvate thereof.

2. The chalcone derivative, salt or solvate according to claim 1, wherein in the formula (1), R$^1$ represents a hydroxyl or lower alkoxyl group, one of R$^2$, R$^3$, R$^4$ and R$^5$ is a carboxyl, cyano, alkyloxycarbonyl, tetrazolyl, —CONHR$^7$ or —O(CH$_2$)$_n$R$^8$, and the remaining groups of R$^2$ to R$^5$ may be the same or different and are independently hydrogen, halogen, hydroxyl, lower alkyl or lower alkoxyl.

3. A cys-leukotriene(cys-LT) receptor antagonist composition comprising an effective amount to antagonize the cys-leukotriene receptor of the chalcone derivative, salt of solvate as defined in claim 1 or claim 2.

4. An antiallergic agent composition comprising an effective amount to function as an antiallergic agent of the chalcone derivative, salt or solvate as defined in claim 1.

5. A pharmaceutical composition comprising the chalcone derivative, salt or solvate as defined in claims 1 or 2 and a pharmacologically acceptable carrier.

6. A method of treating an allergic disease of a person, which comprises administering to said person an effective amount for the treatment of the allergic disease of the chalcone derivative, salt or solvate as defined in claim 1 or 2.

7. A method for treating a person in need treatment with a cys-leucotriene receptor antagonist which comprises administering to said individual an amount effective as a cys-leucotriene receptor antagonist of the chalcone derivative, salt or solvate as defined in claim 1 or claim 2.

8. The chalcone derivative, salt or solvate according to claim 1 or 2, which is 5'-carboxy-2'-hydroxy-2-{(2-quinolyl)methoxy}-chalcone, 5'-ethoxy-carbonyl-2'-hydroxy-4-{(2-quinolyl)methoxy}chalcone, 2'-n-butoxy-5'-carboxy4-(2-quinolylmethoxy)chalcone, 4'-carboxy-3-{(1-ethoxyethylbenzimidazol-2-yl) methoxy}-2'-hydroxychalcone or 5'-cyano-2'-hydroxy-3-{(2-quinolyl)-methoxy}chalcone.

* * * * *